(12) United States Patent
Aiken

(10) Patent No.: US 8,217,191 B2
(45) Date of Patent: Jul. 10, 2012

(54) PROCESS FOR INTEGRATED CO-PRODUCTION OF HYDROGEN PEROXIDE AND EPOXIDIZED ESTERS

(76) Inventor: John E. Aiken, Monroeville, PA (US)

( * ) Notice: Subject to any disclaimer, the term of this patent is extended or adjusted under 35 U.S.C. 154(b) by 447 days.

(21) Appl. No.: 12/613,012

(22) Filed: Nov. 5, 2009

(65) Prior Publication Data

US 2010/0113809 A1 May 6, 2010

Related U.S. Application Data

(60) Provisional application No. 61/198,343, filed on Nov. 5, 2008.

(51) Int. Cl.
*C07D 301/12* (2006.01)
(52) U.S. Cl. ...................... 549/531
(58) Field of Classification Search ............ 549/531
See application file for complete search history.

(56) References Cited

U.S. PATENT DOCUMENTS

| | | | |
|---|---|---|---|
| 2,158,525 A | 5/1939 | Reidl et al. | |
| 2,215,883 A | 9/1940 | Reidl et al. | |
| 2,895,966 A | 7/1959 | Ault et al. | |
| 4,302,435 A | 11/1981 | Gosser | |
| 4,303,632 A | 12/1981 | Gosser | |
| 4,825,013 A | 4/1989 | Cochran et al. | |
| 5,166,372 A | 11/1992 | Crocco et al. | |
| 5,214,168 A | 5/1993 | Zajacek et al. | |
| 5,254,326 A | 10/1993 | Leyshon et al. | |
| 5,463,090 A | 10/1995 | Rodriguez et al. | |
| 5,643,501 A | 7/1997 | Buan et al. | |
| 6,822,103 B2 | 11/2004 | Escrig et al. | |
| 7,071,343 B2 | 7/2006 | Daute et al. | |
| 2007/0261294 A1 | 11/2007 | Aiken | |

FOREIGN PATENT DOCUMENTS

WO 0198404 12/2001

OTHER PUBLICATIONS

Wickson, Edward J., et; Handbook of Polyvinyl Chloride Formulating, (John Wiley & Sons), pp. 253-273, (1993).

*Primary Examiner* — Bernard Dentz
(74) *Attorney, Agent, or Firm* — James Ray & Assoc.

(57) ABSTRACT

A process for the integral production and reactive consumption of hydrogen peroxide combines oxidation of a high-boiling secondary alcohol to form hydrogen peroxide and the ketone analog, recycle of a hydrogenated ketone/alcohol stream to the oxidation step, and epoxidation of unsaturated fatty acid esters utilizing a gaseous hydrogen peroxide stream as it is produced. The epoxidized esters are known to have desirable characteristics for use as plasticizers and similar products.

10 Claims, 3 Drawing Sheets

PROCESS FOR INTEGRATED CO-PRODUCTION OF HYDROGEN PEROXIDE AND EPOXIDIZED ESTERS

CROSS REFERENCE TO RELATED APPLICATION

This patent application is related to and claims priority from U.S. Provisional Patent Application Ser. No. 61/198,343 filed Nov. 5, 2008.

FIELD OF THE INVENTION

The present invention is related to the field of the production and use of hydrogen peroxide. More specifically, the present invention is related to the integration of a process for the production of hydrogen peroxide with the production of epoxidized esters.

BACKGROUND

It is known in the art of lubricant additives and plasticizers for polyvinyl chloride (PVC) that epoxidized fatty acid esters exhibit very desirable properties, especially when there is a moderately high degree of unsaturation within the starting fatty acid chain. After epoxidation, the "oxirane" value is a key factor correlating significantly to performance. This is the weight ratio of the oxygen atoms added across the double bonds, usually chemically depicted as:

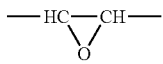

See for example Wickson, Edward J., ed; *Handbook of Polyvinyl Chloride Formulating*, (John Wiley & Sons), pgs 253-273. Performance characteristics of various epoxy plasticizers have been detailed on pages 258 through 271 in the Wickson book. Table 7.9 in Wickson provides a useful summary of relative performance characteristics. Epoxidized monoesters, such as octyl epoxytallate, exhibit some favorable plasticizers properties, especially low-temperature flex and desirable plastisol rheology, but are not so good in other respects. According to the data (Table 7.9 in Wickson), the bis-epoxy esters appear to offer the best overall blend of performance attributes. Ignoring the cost rating relevant to the publication period, it is near the best in almost all categories. Table 7.8 in Wickson indicates even unexpected good performance in plastisols. Table 7.3 in the reference presents evidence that bis-epoxides can offer performance as good as or better than di-isodecyl phthalate (DIDP). In addition, it is stated on page 262 of Wickson that bis-epoxides provide superior resistance to spew in the critical "window exposure test".

The oxirane percent also appears to be a factor to consider for certain performance attributes, and that can be varied and controlled by the selection of the fatty acids used in building the bis-epoxide molecules. With epoxidized soybean oil (ESO), one is limited to whatever the soybean oil allows. On the other hand, if one isolates then epoxidizes an isononyl ester of linolenic acid, the resultant product has almost an 11 percent oxirane content. Certain seeds, flax and camelina for example, contain a relatively high percentage of linolenic acid glycerides. The very common methanolysis to produce biodiesel offers a ready source of fatty acid monoesters that can be distilled into the desired fractions.

World Patent Application WO0198404 also provides some useful comparisons of properties for various epoxy plasticizers. They call the one bis or diester "epoxidized propylene glycol disoyate". The viscosity for this diester plasticizer at ~180 cP is quite favorable compared to ~440 cP for ESO (a fatty acid triester). This facilitates cold weather handling and also fusion with the PVC powder. U.S. Pat. No. 5,643,501 also reports exceptional performance in plasticized PVC from essentially the same material, which is referred to as a secondary stabilizer that the '501 patent calls propylene glycol bis(epoxy oleate).

Besides the bis-epoxides, epoxidized monoglyceride diacetates have been shown to provide some favorable plasticizer properties. See, for example, U.S. Pat. Nos. 2,895,966, and 7,071,343. The performance data available is not nearly as extensive for the monoglyceride diacetates as for the bisepoxides. Actually, epoxidized diglyceride monoacetates would be structured molecularly much like the bis-epoxides.

While these bis-epoxide and glyceride-acetate plasticizers and their favorable performance have been known and offered commercially for many years, extensive commercialization has presumably been hampered mostly by cost considerations, but with record crude oil prices appearing in 2007, that situation is shifting. The doubling of U.S. biodiesel capacity in 2007 alone has made methyl esters of a few types of fatty acids readily available in large quantities in a very competitive marketplace. Meanwhile, a potential major use of the byproduct glycerin has emerged in the form of propylene glycol processes. Epoxidized vegetable oils have long had important industrial uses, but relatively high viscosity and a tendency to exude from plasticized PVC has limited their use as primary plasticizers.

While favorable performance is an important consideration for commercial use, achieving widespread use as a commodity plasticizer depends greatly on the cost relative to competing products of similar performance. In the overall economics of epoxy ester production, an economical source of hydrogen peroxide is a very important factor, as it is a key reactant in the epoxidation reaction. It typically will account for about 20 wt % of the raw material. Besides cost, storage and transportation of the required concentrated hydrogen peroxide solutions presents significant safety concerns, especially in light of recent terrorist threats. The fatty acid portion of the molecules still accounts for approximately 80 percent by weight, so that cost is of course a major consideration. As previously mentioned, biodiesel fuel or fractions thereof can be an economic source of the fatty acid portion, particularly if made from lower-value reclaimed waste feedstocks instead of virgin refined vegetable oils.

The most prevalent process for production of hydrogen peroxide involves the cyclic oxidation and reduction of a working compound such as an alkyl anthrahydroquinone with concurrent formation of hydrogen peroxide and the corresponding anthraquinone. Two of the earliest disclosures of this technology were by Reidl in U.S. Pat. Nos. 2,158,525 and 2,215,883. The oxygen atoms in the hydrogen peroxide molecule ultimately come from oxygen in the atmosphere, but a regenerable oxygen carrier molecule is typically needed to generate the hydrogen peroxide molecules. The anthraquinone or other oxygen carrier is subsequently hydrogenated to regenerate the starting anthrahydroquinone, which is then recycled to oxidation. Although the bulk of the reagent is recycled continuously through the process, it is necessary to provide a make-up stream to replace the inevitable losses of regenerable working compound in the process. This issue of formation and removal of inert byproducts was addressed by Sethi in U.S. Pat. No. 4,824,609. The ethyl anthraquinone used in the most common industrial process is an expensive material, so even a small make-up stream to the recycle can be a significant expense. In addition, there is significant working capital tied up as part of the in-process inventory.

U.S. Pat. Nos. 4,897,252, 5,254,326, and others by the same inventors, describe a similar process that uses oxidation of a secondary alcohol, methylbenzyl alcohol (MBA), to make hydrogen peroxide ($H_2O_2$), and byproduct acetophenone results. In the process, the byproduct acetophenone is hydrogenated back to MBA, which is subsequently recycled to oxidation. The methylbenzyl alcohol is a much less expensive material than the substituted anthraquinones; however, the recovery and separation steps of the MBA-based process are considerably involved, with steps of stripping, extraction, and distillation being necessary to make it practical. This is a consequence of the secondary alcohol with a normal boiling point near 200 C having a significant volatility relative to the hydrogen peroxide, which has an atmospheric boiling point close to 150 C. Although the MBA/acetophenone process is substantially different than that of the instant invention, favorable oxidation conditions for secondary alcohols have been disclosed and are incorporated herein by reference.

Epoxidation of ethylenically unsaturated compounds, specifically light olefins such as ethylene and propylene, in combination with hydrogen peroxide production, is discussed extensively in the prior art literature. Among these are a series of patents assigned to Arco Chemical Technology, including U.S. Pat. Nos. 4,897,252, 5,166,372, 5,214,168, and 5,463,090. The hydrogen peroxide produced in the processes of these three patents is fed, still combined with its working solution, to the epoxidation reactor along with the olefin substrate, typically propylene. Consequently, an additional separation step is needed to remove the product from the regenerable working material and other epoxidation reaction constituents. This necessitates additional equipment and expense. The Arco process is tailored to light olefins only, ones yielding product which can be stripped out readily after the epoxidation.

Similarly, an integrated process for epoxidation of lighter olefins is disclosed in U.S. Pat. No. 6,822,103. Highly corrosive HBr is used in generation of the hydrogen peroxide by feeding oxygen-containing gas into a predominately volatile methanol mixture. The resulting 9.3% hydrogen peroxide solution was used for epoxidation of either octene or propylene in the presence of a volatile solvent. There is no indication that solvent recoveries and separation would be commercially feasible. As with the Arco process, light olefins are the main target.

U.S. Pat. No. 4,303,632 by Gosser discloses promising oxidation results for another secondary alcohol system, that of diphenylcarbinol (benzhydrol) and benzophenone. However, under the conditions described by Gosser, the reported yields were far from what would be practical for commercialization. The viability and conditions for the necessary hydrogenation of benzophenone to diphenylcarbinol were disclosed in U.S. Pat. No. 4,302,435. However, it is not obvious how the benzophenone system could be made practical, and there is no knowledge of any later efforts to further develop or commercialize this method. The initial charge and makeup benzophenone material are relatively inexpensive.

SUMMARY OF THE INVENTION

The present invention provides an improved combined process for the manufacture of hydrogen peroxide by the oxidation of high-boiling secondary alcohols integrated with epoxidation of unsaturated fatty acid esters. For the hydrogen peroxide generation, a high-boiling secondary alcohol is air oxidized, producing hydrogen peroxide and a ketone analog of the alcohol. The hydrogen peroxide is stripped out by a recycling gas stream and injected into an epoxidation reactor. The ketone/alcohol recycle stream is subjected to hydrogenation to reduce the bulk of the ketone analog back to the secondary alcohol for recycle to the oxidation step. In the epoxidation reactor, the gaseous hydrogen peroxide is sparged into a solution of unsaturated fatty acid esters and acetic acid, and the liquid is contacted with an acidic catalyst.

In a preferred embodiment of the present invention, the fatty acid esters being epoxidized are diesters made by transesterification of unsaturated fatty acid methyl esters with a glycol. In the preferred embodiment of the invention, the secondary alcohol is diphenylcarbinol and the ketone analog is benzophenone.

OBJECTS OF THE INVENTION

It is, therefore, one of the primary objects of the present invention to provide a process with very favorable capital and operating costs for high-volume commercial production of epoxidized ester products known for good performance as plasticizers or lubricant additives.

Another object of the present invention is to improve the safety of processes for reacting hydrogen peroxide to produce epoxy compounds without the need to concentrate and store dangerous concentrations of hydrogen peroxide.

Still another object of the present invention is to provide a commercially attractive route for producing useful epoxidized fatty acid esters almost entirely from renewable agricultural products.

Yet another object of the present invention is to provide an economically attractive process for most oxirane additions to unsaturated compounds of greater than 20 carbon atoms in size.

An additional object of the present invention is to provide a process utilizing hydrogen peroxide generated concurrently and primarily as a gas easily separated from a moderately-priced working solution without involving a considerable amount of water.

Yet another object of the present invention is to provide a process generating hydrogen peroxide made from a moderately-priced working solution thus reducing expenses associated with the most-common working solution.

In addition to the various objects and advantages of the present invention described with some degree of specificity above it should be obvious that additional objects and advantages of the present invention will become more readily apparent to those persons who are skilled in the relevant art from the following more detailed description of the invention, particularly, when such description is taken in conjunction with the attached drawing figures and with the appended claims.

DETAILED DESCRIPTION OF THE INVENTION

The invention comprises an improved process for the coproduction of hydrogen peroxide and high-boiling epoxidized esters combining air oxidation of a secondary alcohol and epoxidation of unsaturated esters using the co-produced hydrogen peroxide. In its most general sense, the invention comprises the integration of the production of hydrogen peroxide with the production of epoxidized compounds. A novel feature of the proposed process is the ability to take advantage of easy separation of the peroxide from a moderately-priced high-boiling working solution without an additional separation involving the desired product stream.

Figure 1:
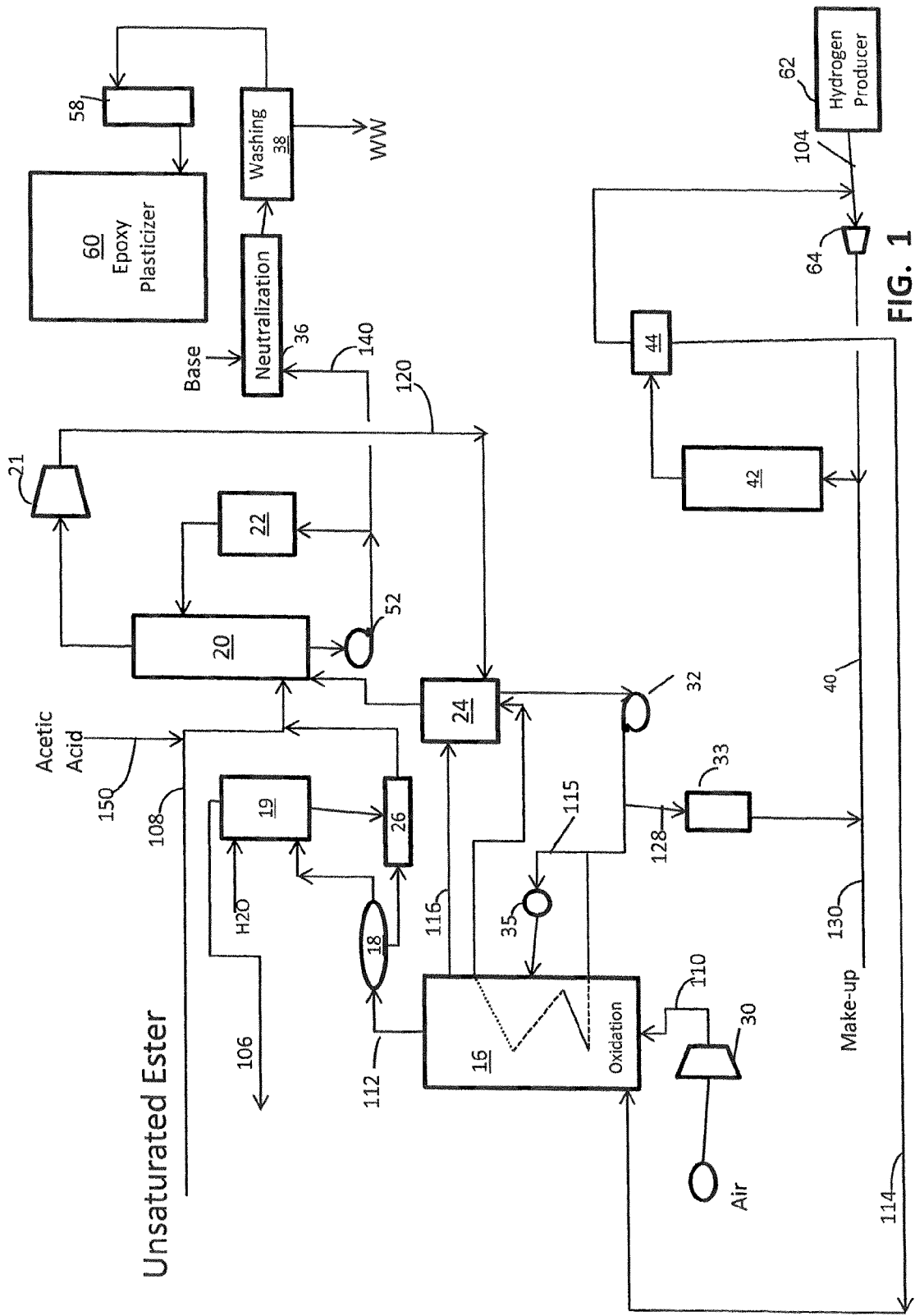
FIG. 1 is a block flow schematic diagram illustrating an exemplary embodiment of the present invention of integration of hydrogen peroxide production and epoxidation of unsaturated esters.

A process for concurrent production of hydrogen peroxide, incorporating oxidation of a secondary alcohol, and epoxidized ester according to the current invention will now be described in detail with reference to exemplary FIG. 1, which starts with providing any unsaturated mono, di, or tri-ester feed material, or combinations thereof, having a normal boiling point in excess of 200 C, as stream 108, which is subsequently fed to an epoxidation reactor 20 described in more detail later. Intermediate temporary storage will obviously be employed for holding the feed material, but is not shown here for simplicity.

Hydrogen peroxide is the essential ingredient for adding oxygen to the carbon-carbon double bonds to form the oxirane structures (Epoxidation) in the epoxidized products. This peroxide is produced substantially concurrent with epoxidation in oxidation reactor 16 which is nearly full of liquid with compressed air sparged in from compressor 30 via conduit 110. Although depicted as continuous operation, batch operation is not ruled out. Typical conditions within oxidizer 16 would be a temperature of 130 C and 570 kPa as revealed in the aforementioned Arco patents; however, a wide range of conditions could be acceptably employed provided the temperature is at least 70 C to stay above the melting point of diphenylcarbinol. The regenerable reagent can be an anthraquinone material, but preferably is a high-boiling secondary alcohol such as diphenylcarbinol (benzhydrol) as disclosed in U.S. Pat. No. 4,303,632 by Gosser, and incorporated herein by reference. However, under the conditions described by Gosser, the reported yields were far from ideal for practical commercialization. Although not obvious, the pressures, temperatures, residence times, and water concentrations disclosed in the aforementioned Arco patents, such as U.S. Pat. Nos. 4,897,252 and 5,254,326, could be expected to produce better results than Gosser's with a similar but high-boiling secondary alcohol, diphenylcarbinol. A portion of the teachings of these two patents, U.S. Pat. Nos. 4,897,252 and 5,254,326, for oxidation conditions are incorporated herein by reference thereto. The normal boiling points for diphenylcarbinol and benzophenone are 298 C and 306 C respectively, which are considerably higher than the 202 C boiling point for the acetophenone utilized in the process of the Arco patents. This difference greatly simplifies the downstream recovery and recycle steps, as will be evident herein later when compared to the aforementioned Arco patents. Benzophenone, the ketone analog of diphenolcarbinol, is designated as the most preferred ketone and diphenylcarbinol as the most preferred alcohol, but it should be recognized that no restriction to these two is implied. To achieve the recovery advantage, the secondary alcohol should have a normal boiling point in excess of 220 C. The liquid feed to oxidizer 16 is a predominately diphenylcarbinol recycle stream 114 generated by hydrogenation of byproduct benzophenone, with makeup benzophenone 130 added as needed.

Removing the heat produced by the oxidation reaction 16 is important, and is accomplished by a combination of at least two of various means including evaporation of water and hydrogen peroxide into the gas stream, circulation of an effluent side stream 115 through a water-cooled heat exchanger 35, and/or by flash cooled liquid from pump 32 flowing through internal coils. Not all of these cooling means are necessary. Gaseous effluent 112 from the oxidation is cooled to condense much of any hydrogen peroxide vapor in the spent air effluent. Any residual peroxide remaining in the gas stream can be absorbed into water in scrubber 19 before the spent air 106 is vented to the atmosphere or a tertiary treatment unit. The recovered peroxide and any accompanying water are collected and stored briefly in small volume in vessel 26 for subsequent addition to the epoxidation reactor 20.

The air feed 110 has been boosted in pressure with compressor 30 to sparge into the oxidizer 16. The organic stream comprising benzophenone and some diphenylcarbinol is removed from the oxidizer 16 via line 116 and sent to a stripping pot or column 24, wherein hydrogen peroxide dissolved in the organic stream is stripped out into a recirculating inert gas stream 120 and sent to the epoxidation reactor 20, wherein it is absorbed into and reacts with the unsaturated segments of the FADE and/or C6-C10 alkyl monoester of unsaturated fatty acids to form the desired epoxy compounds. Stripped liquid stream 115 is boosted in pressure by pump 32 and a slip stream 128 is briefly held in surge tank 33 before being combined with any needed make-up 130 to create hydrogenation feed stream 40.

Make up ketone analog (benzophenone) 130 is added to the recycle alcohol stream 114 in the hydrogen peroxide process as necessary. Preferably, the make up stream 130 is added to the recycle stream 40 prior to the hydrogenation step 42 as illustrated, but there are alternative locations which would be acceptable. The viability and conditions for the hydrogenation of benzophenone to diphenylcarbinol were disclosed in U.S. Pat. No. 4,302,435, and are incorporated herein by reference. Briefly summarizing, a benzophenone-rich stream is passed in liquid phase along with gaseous hydrogen over a bed of supported Lindlar catalyst at about 120 C and 500 kPa pressure. It is not essential to obtain a high degree of conversion per pass as a blend of the ketone analog and secondary alcohol can be fed back into the oxidation reactor, but the hourly rate of moles hydrogenated should be nearly equal to those of alcohol oxidized. The hydrogenation effluent is phase separated in vessel 44 with the hydrogen recycling back to hydrogenation 42 and the diphenylcarbinol-rich stream 114 being fed back into oxidation. Pumps and compressor 64 are used as needed to boost stream pressures.

As previously mentioned, the gaseous hydrogen peroxide stream from stripping unit 24 is fed into an epoxidation reactor 20 along with unsaturated fatty acid esters stream 108. In addition, aqueous hydrogen peroxide solution from vessel 26 will typically be metered in for at least a portion of the epoxidation step. While not excluding continuous mode, batch-wise operation for the epoxidation is commonly preferred, so at least two epoxidation trains will be employed so as to permit substantially continuous operation of the oxidation with minimal surge volume of hydrogen peroxide. With the aid of some water from the aqueous peroxide addition, the reaction mix in reactor 20 absorbs nearly all the hydrogen peroxide from the recycling gas stream 120, which is recycled back to the stripping unit 24 with the aid of compressor 21. A catalytic amount of acetic acid 150 is also introduced either directly into reactor 20 or into ester feed stream 108. While addition of a fractional percent of a strong acid catalyst is an option, it is preferable to circulate the contents of the reactor 20 through a supported acidic resin bed 22 with the aid of a pump 52. Typically, either source of acid catalyst is a sulphonic-acid variety. The acetic acid and hydrogen peroxide combine to form the more reactive peracetic acid species within the resin beads, which tend to exclude the desired epoxy molecules from contact with the potentially degrading strong acid. When time and analyses indicate that the epoxidation is nearing completion, all feeds are stopped and circulation continues for several additional minutes until reaction is substantially complete. The crude epoxidation product is then transferred out through conduit 140 to the neutralization step 36, and washing step 38, both steps likely being performed in the same vessel. A base is added at the neutralization step 36 to tie up residual acetic acid, and the resulting salts are washed out at 38. The aqueous material 142 is decanted off and routed to a wastewater treatment facility. The washed product 144 is subjected to at least one additional treatment operation 58 before entering into product storage 60. Examples of treatment steps 58 are vacuum stripping of water and volatile contaminants, and adsorption of trace impurities on a fixed bed of activated carbon, fuller's earth, molecular sieve, or resin. In lieu of a fixed bed, slurring with powder followed by filtration constitutes another acceptable method of treatment.

Figure 2:
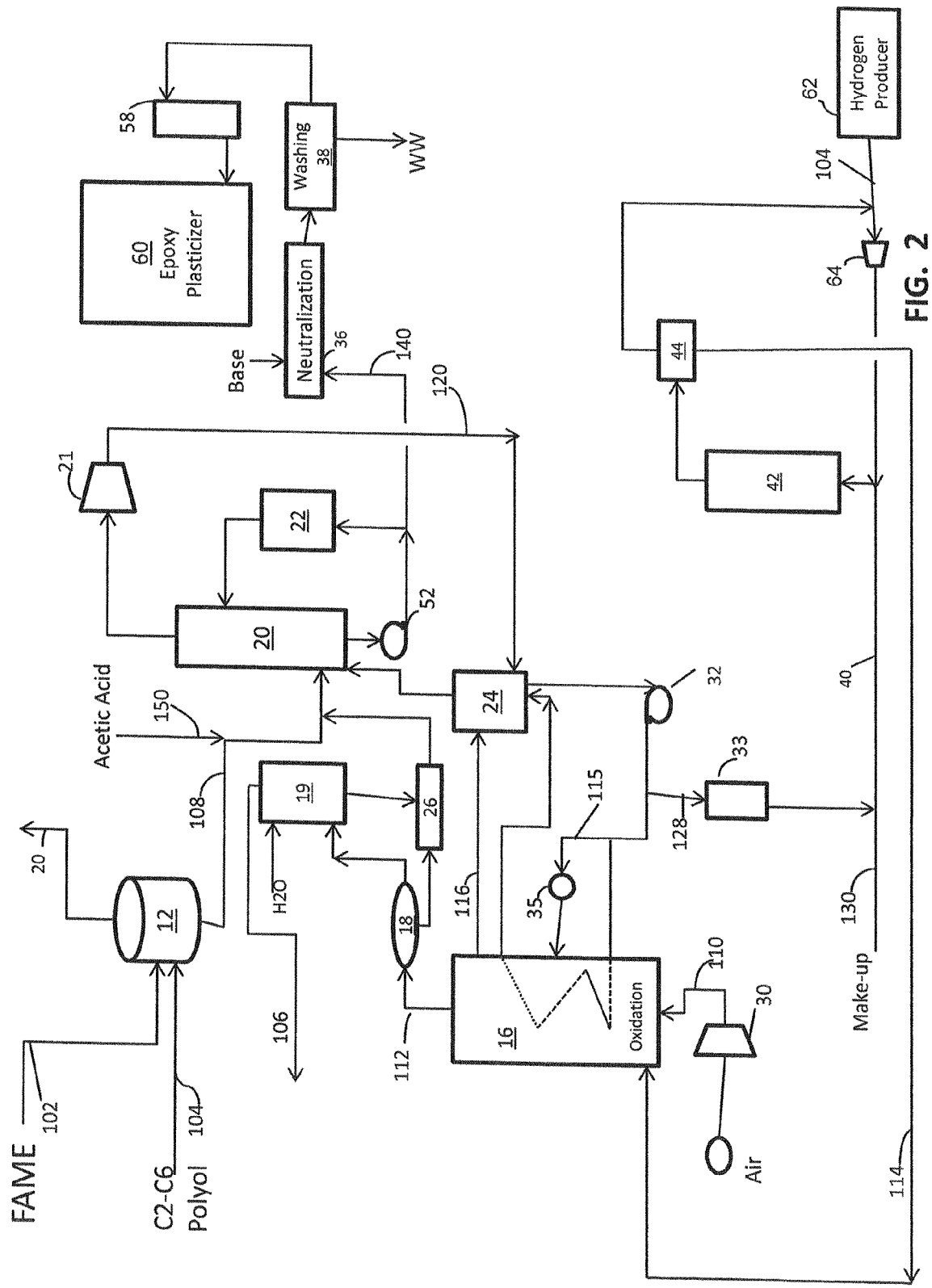
FIG. 2 is a block flow schematic illustrating the present process invention combined with production of a fatty acid diester feed material.

An alternative method for manufacture of epoxidized ester plasticizer incorporating oxidation of a secondary alcohol with ester epoxidation according to the current invention will now be described in detail with reference to exemplary FIG. 2, which includes an optional section for production of a fatty acid diester. A partially unsaturated fatty acid methyl esters (FAME) stream 102 and a C2 to C6 glycol 104 are fed to a transesterification reactor 12. The unsaturated FAME material is to have an iodine value of at least 100, preferably over 150 for certain products. The source of this FAME with high iodine value will preferably be a distillation fraction out of biodiesel production, with the fatty acid portion being predominately molecules with either two or three unsaturated carbon-carbon double bonds, for example, linoleic and linolenic acid. This transesterification reaction is typically, but not necessarily, conducted batchwise with heating and stirring, liberating methanol or other low-boiling alcohol as a byproduct vapor 21, which is condensed and recycled to a biodiesel process, most commonly the one manufacturing the FAME stream. Given the high volatility of methanol, this reaction will typically go to a high degree of completion in under two hours with little excess glycol and a fraction of a percent of a catalyst. Excess glycol, typically propylene glycol, can be vacuum stripped out to an advantageous level, as desired. The hydroxyl number can be ascertained readily as the stripping proceeds to determine the end point for this stage. It is envisioned that multiple batch reactors in parallel would be employed in a commercial production plant.

This sort of transesterification is a very common type of process and is described in a multitude of prior art including that of manufacturing polymeric plasticizers. It is not an essential part of the present invention, and is presented here as merely an economical manner of obtaining a diester feed material. In some instances, a C6 to C10 alkyl fatty acid monoester may constitute a portion or all of the unsaturated fatty ester feed. Also, a triglyceride with some degree of unsaturation, such as soybean oil, would also be an acceptable feed. Yet another would be a cyclohexene dicarboxylic acid ester, such as that formed from a Diels-Alder reaction of butadiene and maleic anhydride.

The fatty acid diester (FADE), monoester, triester, or combinations thereof, stream 108, is subsequently fed to an epoxidation reactor 20, as described previously. Intermediate temporary storage will obviously be employed for holding the FADE, but is not shown here for simplicity. Unsaturated fatty acid monoesters of a C6 or higher alcohol can optionally replace up to 100% of the FADE stream 108, depending on desired properties of the final product. Lower molecular weight plasticizers would be produced, but these also are known to exhibit useful plasticizing properties for certain applications. One exemplary source of these monoesters would be from fractional distillation of biodiesel product using in part a water immiscible alcohol for pretreatment of free fatty acid containing feeds, as taught in U.S. Patent Application 2007/0261294 and incorporated herein by reference, with subsequent fractional distillation from the biodiesel product. Beginning with step 20, the processing method is the same as described previously for FIG. 1.

Figure 3:
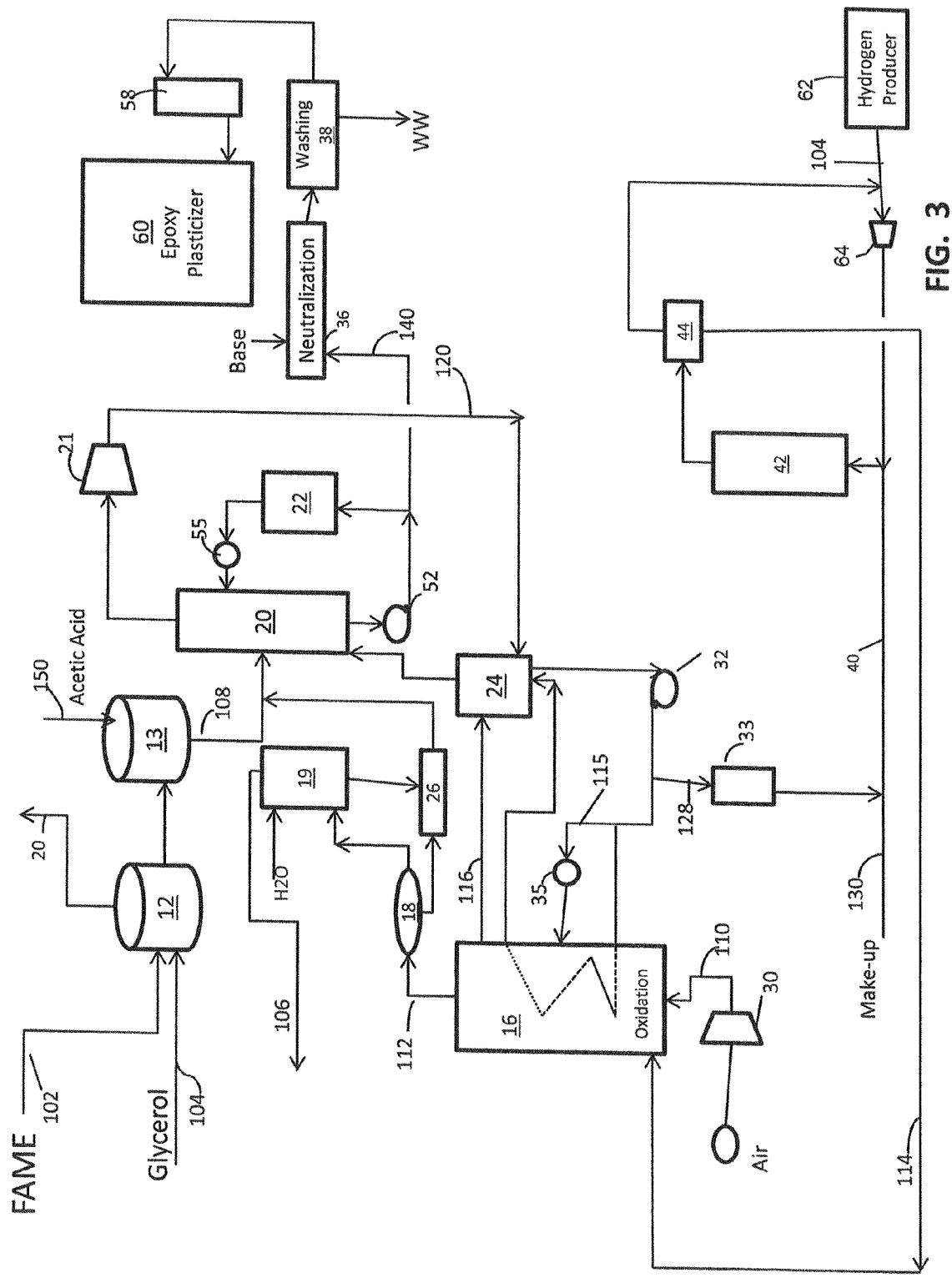
FIG. 3 provides a block flow diagram of an alternative embodiment utilizing an alternative fatty acid ester to that shown in FIG. 2.

FIG. 3 provides another alternative embodiment of the present invention. It is very much like that disclosed in FIG. 2, except that the unsaturated ester 108 being fed to epoxidation 20 is made up of mono and di-glyceride acetate molecules. At transesterification step 12, the methanol in the unsaturated FAME feed 102 is displaced by glycerol 104. At step 13, the predominately monoglyceride intermediate is then esterified with acetic acid 150 to produce the glyceride-acetate feed 108 for epoxidation at step 20. The 108 stream also provides the acetic acid for helping to catalyze the epoxidation. Otherwise, the processing is as described above for FIG. 1.

While a presently preferred and various alternative embodiments of the present invention have been described in sufficient detail above to enable a person skilled in the relevant art to make and use the same, it should be obvious that various other adaptations and modifications can be envisioned by those persons skilled in such art without departing from either the spirit of the invention or the scope of the appended claims.

What is claimed is:

1. An integrated method for the manufacture of epoxidized esters comprising:
    a) combining an oxygen-containing gas stream and a liquid secondary alcohol having a boiling point greater than 220 C;
    b) reacting said secondary alcohol and said oxygen-containing stream to form hydrogen peroxide and a ketone analog;
    c) hydrogenating said ketone analog to reform said liquid secondary alcohol;
    d) recycling said liquid secondary alcohol to said combining step;
    e) stripping said hydrogen peroxide from said ketone analog to form a gaseous peroxide stream;
    f) contacting said gaseous peroxide stream with at least one unsaturated fatty acid ester; and
    g) reacting said fatty acid ester and said gaseous peroxide stream in the presence of acetic acid and a sulphonic acid catalyst to form such epoxidized esters.

2. The integrated method, according to claim 1, wherein said unsaturated fatty acid ester is a product of reacting at least one fatty acid lower alkyl ester with at least one C2-C6 polyol.

3. The integrated method, according to claim 2, wherein said C2-C6 polyol is at least one of propylene glycol and glycerol.

4. An integrated method for the manufacture of epoxidized esters comprising:
    a) providing a source of oxygen-containing gas and a pressure vessel;

b) generating a hydrogen peroxide reactant stream by steps including:
  (i) providing a first oxidation liquid reaction mixture of greater than 50 weight percent of a secondary alcohol to said pressure vessel;
  (ii) contacting within said pressure vessel said oxygen-containing gas with said first oxidation reactor feed under predetermined conditions sufficient to oxidize at least half of said secondary alcohol to hydrogen peroxide and byproduct ketone analog;
  (iii) separating effluent of said oxidation reactor vessel into a first gaseous and a first liquid effluent stream;
  (iv) stripping hydrogen peroxide from said first liquid effluent stream with a recycling gas stream to form a resultant gas stream and a stripped liquid stream;
  (v) combining said resultant gas stream with said second gaseous stream to form said hydrogen peroxide reactant stream;
  (vi) contacting said first gaseous stream with an aqueous solution to form an aqueous peroxide stream;
  (vii) injecting a predetermined cooled portion of said stripped liquid stream back into said oxidation reaction vessel;
  (viii) providing an hydrogenation reaction vessel having a source of super-atmospheric hydrogen gas;
  (ix) hydrogenating at least half of said ketone analog in a portion of said stripped liquid stream into an hydrogenated ketone stream containing between 20 and 80 mole percent of said secondary alcohol;
  (x) recycling said hydrogenated ketone stream to Step 4-b-(i) to provide said secondary alcohol
b) commingling an unsaturated fatty acid ester with said aqueous peroxide stream and catalytic amounts of acetic acid to provide a liquid epoxidation reactor charge;
c) reacting an unsaturated fatty acid ester with said hydrogen peroxide reactant stream in the presence of a preselected acidic catalyst and acetic acid at predetermined conditions to form an epoxidized product;
d) venting a third gaseous stream continuously during course of said reacting of fatty acid ester and boosting pressure of said third gaseous stream to form said recycle gas stream in step 4-a)(vii);
e) stopping the epoxidation reaction based upon preselected criteria;
f) neutralizing acidic components of the stopped epoxidation product by mixing with a base;
g) recovering a crude epoxidized product from said neutralized reaction product;
h) treating said crude epoxidized product over at least one of drying, ion-exchange, adsorption, and decolorizing beds of solids to produce such epoxidized ester.

5. An integrated method for manufacture of epoxidized fatty acid esters comprising the steps of:
a) generating a hydrogen peroxide reactant stream by steps including:
  (i) providing a first oxidation liquid reaction mixture of greater than 50 weight percent secondary alcohol;
  (ii) contacting said liquid secondary alcohol with a compressed air stream in an oxidation reactor vessel at a first predetermined temperature and first predetermined pressure;
  (iii) feeding continuously at least one stream having greater than 50 weight percent of secondary alcohol into said first oxidation reactor vessel;
  (iv) oxidizing at least half of said secondary alcohol to form hydrogen peroxide and a ketone analog;
  (v) withdrawing at effluent of said oxidation reactor vessel a first gaseous and a first liquid effluent stream;
  (vi) cooling first gaseous effluent stream from said first oxidation reactor vessel thereby creating a second gaseous and second liquid stream;
  (vii) reducing pressure of said first liquid effluent stream substantially below said first predetermined pressure thereby forming a second gaseous and a second liquid effluent stream;
  (viii) stripping hydrogen peroxide from said second liquid effluent stream with a recycling gas stream to form a third gaseous stream;
  (ix) combining said third gaseous stream with said second gaseous stream to form said hydrogen peroxide reactant stream and a stripped liquid stream;
  (x) contacting said first gaseous stream with an aqueous solution to form at least an aqueous peroxide stream;
  (xi) injecting a predetermined portion of said second effluent stream back into said oxidation reaction vessel;
  (xii) hydrogenating at least half of said ketone analog to said secondary alcohol and forming an hydrogenated ketone stream; and
  (xiii) recycling said hydrogenated ketone stream to Step 5-a-(ii) to provide substantially all of said secondary alcohol
b) commingling an unsaturated fatty acid ester with said aqueous peroxide stream and catalytic amounts of acetic acid to provide a liquid epoxidation reactor charge;
c) reacting batch-wise said liquid epoxidation charge with said primary hydrogen peroxide reactant stream in the presence of a preselected acidic catalyst at a predetermined temperature to form an epoxidized product;
d) venting a third gaseous stream continuously during course of said batchwise reaction and boosting pressure of said third gaseous stream to form said recycle gas stream in step 1-a-(vii);
e) stopping said batch-wise reaction based upon preselected criteria;
f) neutralizing acidic components of said stopped epoxidation product by mixing with a base;
g) separating the neutralized acid salts from said epoxidized ester;
h) treating the separated epoxidized ester over at least one of drying, ion-exchange, adsorption, and decolorizing beds of solids.

6. The integrated method, according to claim 4, wherein said secondary alcohol has a normal boiling point greater than 220 C.

7. The integrated method, according to claim 6, wherein said secondary alcohol is diphenylcarbinol.

8. The integrated method, according to claim 5, wherein said secondary alcohol has a normal boiling point greater than 220 C.

9. The integrated method, according to claim 8, wherein said secondary alcohol is diphenylcarbinol.

10. The integrated method, according to claim 1, wherein said secondary alcohol is diphenylcarbinol and said ketone analog is benzophenone.

* * * * *